United States Patent [19]

Schwesinger

[11] 4,406,291
[45] Sep. 27, 1983

[54] EXHALATION MONITORING APPARATUS

[76] Inventor: Dennis W. Schwesinger, 22708 Rodax St., Canoga Park, Calif. 91304

[21] Appl. No.: 138,071

[22] Filed: Apr. 7, 1980

[51] Int. Cl.³ .............................................. A61B 5/08
[52] U.S. Cl. .................................. 128/728; 128/730; 73/861.43; 73/861.47; 73/861.63
[58] Field of Search ....................... 128/725, 727–730, 128/203.12, 205.23; 73/223, 861.43, 861.47, 861.63

[56] References Cited

U.S. PATENT DOCUMENTS

| 3,718,044 | 2/1973 | Joyce, Jr. et al. | 73/223 |
| 3,875,626 | 4/1975 | Tysk et al. | 73/223 X |
| 3,890,967 | 6/1975 | Elam et al. | 128/205.23 |
| 3,898,987 | 8/1975 | Elam | 128/205.23 |
| 4,121,581 | 10/1978 | Schmader | 128/203.12 |

Primary Examiner—Kyle L. Howell
Assistant Examiner—John C. Hanley

[57] ABSTRACT

An exhalation monitoring apparatus measures and then instantly displays the volume of expired air from a patient. The instrument includes a manifold having a central chamber with an inlet opening for receiving exhaled gas from a patient. The manifold also has attached a flaccid bag so as to allow for the collection of all the exhaled gases without increasing the pressure in the manifold above the ambient air pressure. A venturi is provided in the chamber with an inlet port for connection to a source of driving gas outside the manifold and an outlet port for venting the driving gas outside the manifold. Also provided is an induction port in the throat of the venturi within the chamber for drawing in exhaled gas received in the chamber and flaccid bag. A pressure responsive electrical switch and timing circuit generate a signal constituting a function of the time it takes for the venturi to exhaust all of the exhaled air from the chamber and flaccid bag. This time interval in turn is directly proportional to the volume of exhaled air and thus can be converted to a digital signal indicating such volume in volumetric units.

2 Claims, 3 Drawing Figures

EXHALATION MONITORING APPARATUS

This invention relates generally to monitoring equipment and more particularly to an exhalation monitoring apparatus for measuring and displaying the volume of expired air from a patient.

BACKGROUND OF THE INVENTION

The artificial ventilation and the care of critical respiratory patients in hospitals requires the monitoring of volumes of exhaled air from the patients not only to provide an indication of the effectiveness of sustained life support systems but also as a diagnostic tool. Any such devices should incorporate an appropriate alarm to indicate when critical life support parameters such as respiration change.

Many devices are available in the prior art for determining the tidal volume of exhaled air from a patient during artificial respiration or ventilation. These devices include, for example, two distinct types of volume measuring apparatuses. One such type requires a large chamber or housing sufficient in size as to contain the entire volume of gas being measured at ambient pressures. The other type of apparatus consists of electronic, electro-mechanical or mechanical sensors which measure volume by indirect means.

These above described prior art devices for the most part either perform with low accuracy or require a specially skilled person for their operation. Moreover, the prior art devices, and especially those providing accurate results, are excessively delicate and subject to damage by normal operational environmental conditions. For example, exposure to the high humidity and water particulates naturally involved in collecting exhaled gases is damaging to such prior art devices. Additionally, those devices which use sensors for the indirect measurement of gas volumes experience accuracy distortion due to a dependence upon flow rate as a measuring condition. Since the flow rate of exhaled gases fluctuates widely, prior art devices utilizing sensor technology have performed with low accuracy.

Finally, most prior art instruments which are deemed satisfactory normally require skilled technicians to operate and to read out the desired information.

BRIEF DESCRIPTION OF THE PRESENT INVENTION

With the foregoing considerations in mind, the present invention contemplates an improved exhalation monitoring apparatus which is relatively simple and inexpensive in construction and yet operates with a high degree of accuracy and does not require any particular skill on the part of the operator.

Briefly, the monitoring apparatus of this invention comprises a manifold having a central chamber and an inlet opening for receiving exhaled gas from a patient. A pressure responsive valve means is positioned between the inlet opening and the central chamber responsive to a chamber pressure below ambient pressure to close. A venturi is provided in the chamber and has an inlet port for connection to a source of driving gas outside the manifold. Also the outlet port for the venturi is provided for venting the driving gas outside the manifold. An induction port at the throat of the venturi, in turn, communicates with the chamber of the manifold for drawing in exhaled gas received through the inlet opening. Finally, a pressure responsive means responsive to changes in pressure in the chamber relative to ambient pressure is provided to generate a signal indicative of the volume of exhaled gas received into the chamber.

In a first embodiment of the invention, there is provided a flaccid bag in communication with the chamber for collecting exhaled gas without substantially affecting the ambient pressure. The pressure responsive means takes the form of an electrical switch, timer and digital display wherein the period of time for the venturi to exhaust the exhaled gases from the flaccid bag is measured, this period of time being directly proportional to the volume of the exhaled gases. The volume is thus displayed on the digital display in volumetric units.

In a second embodiment, the exhaled gas is directly drawn from the chamber by the venturi and a change in pressure is monitored during this exhaustion to provide a signal indicative of the flow rate. This signal can be integrated to thus provide an indication of the total volume of exhaled gas.

BRIEF DESCRIPTION OF THE DRAWINGS

A better understanding of this invention as well as further features and advantages thereof will be had by now referring to the accompanying drawings in which.

DETAILED DESCRIPTION OF THE INVENTION

Figure 1:
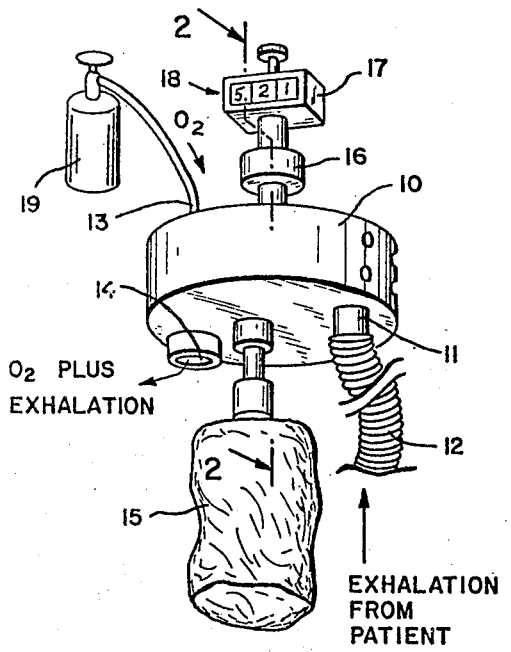
FIG. 1 is a perspective view of a first embodiment of the exhalation monitoring apparatus of the present invention.

Referring first to FIG. 1, the exhalation monitoring apparatus includes a manifold indicated generally at 10 including a central chamber and an inlet opening 11 for receiving exhaled gas from a patient. In this respect, the exhaled gas is passed into the inlet 11 by way of a corrugated tube 12 connected to respiratory or ventilating apparatus associated with the patient.

As will become clearer as the description proceeds, the interior of the manifold 10 also includes a venturi. This venturi is provided with an inlet port indicated at 13 communicating with a source of driving gas such as oxygen outside of the manifold 10. The venturi outlet port is indicated at 14 and will vent the driving gas outside the manifold 10.

In the particular embodiment shown in FIG. 1, there is also provided a flaccid bag 15 which might be made of plastic connected to the manifold 10 and in communication with the interior chamber. This bag serves to collect exhaled gas received within the inlet opening 11 without appreciably affecting the pressure in the chamber.

Shown above the manifold 10 is a pressure responsive means responsive to changes in pressure in the manifold relative to ambient pressure. In the embodiment of FIG. 1, this pressure responsive means includes an electrical switch 16, timer circuit 17 and digital display 18 all indicated schematically in FIG. 1.

Also shown in FIG. 1 is a tank 19 for providing driving gas, such as oxygen, to inlet port 13 for the venturi within the manifold 10.

Figure 2:
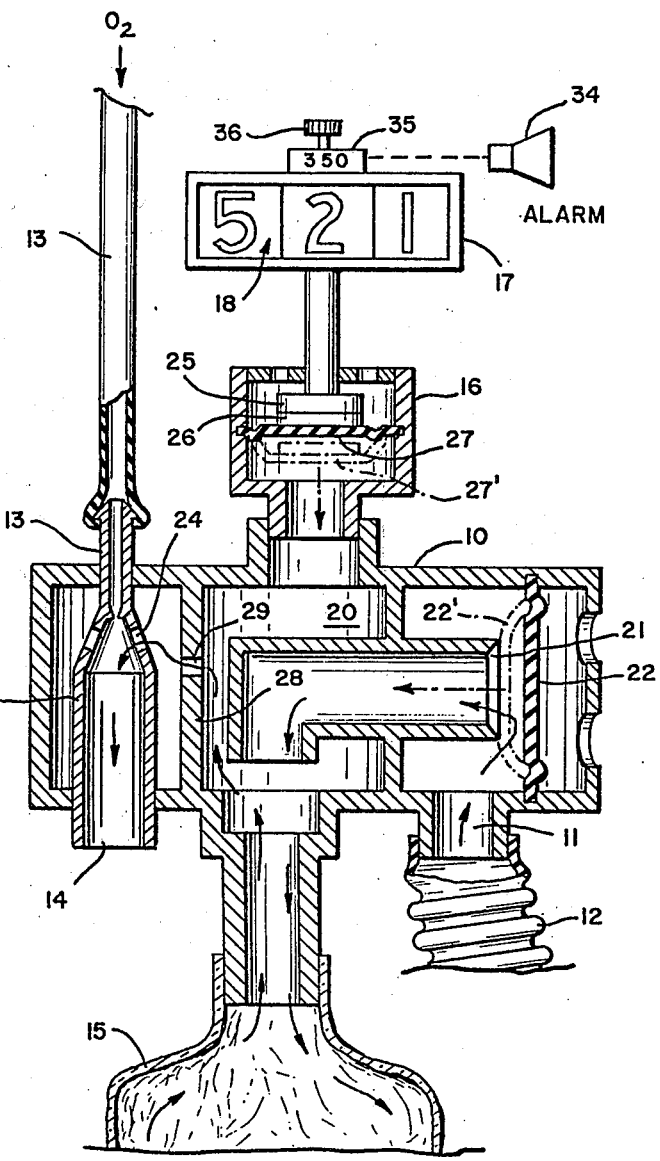
FIG. 2 is a greatly enlarged fragmentary view partly in cross section taken in the direction of the arrows 2—2 of FIG. 1; and, FIG. 3 is a fragmentary cross section of a second embodiment of the invention.

Referring now to the enlarged cross section of FIG. 2, the central chamber within the manifold 10 is indicated at 20. Also shown within the manifold 10 connected between the inlet opening 11 and the chamber 20 is a pressure responsive valve means in the form of a valve seat 21 and flexible diaphragm 22. When the diaphragm 22 seats on the valve seat 21 as indicated by the dotted line position 22', communication between the inlet opening 11 receiving exhaled air and the chamber 20 is cut off.

Referring to the left portion of the manifold 10 of FIG. 2 there is shown the heretofore referred to venturi at 23. Induction ports for this venturi are shown in the throat thereof at 24 in communication with the central chamber 20.

FIG. 2 also illustrates further details of the pressure responsive means briefly referred to in FIG. 1 at 16, 17 and 18. As shown, the switch portion 16 includes a reed switch 25 arranged to be closed by a magnet 26 carried on a diaphragm 27. Diaphragm 27 is subject to the pressure in the central chamber 20 of the manifold 10. A decrease in this pressure below ambient pressure results in the diaphragm 27 being pulled downwardly to the dotted line position shown at 27' thereby removing the magnet 26 from the vicinity of the reed switch 25 so that this reed switch will open. It should be understood that any other equivalent electrical switch means responsive to a change in pressure could be utilized for the structure 16.

While not essential, in a preferred embodiment of this invention, the chamber 20 of the manifold 10 incorporates a partition 28 between the venturi 23 and the interior chamber portion in communication with the flaccid bag 15. Partition 28 is provided with a fixed orifice 29 through which exhaled air is passed to the venturi so that the flow rate of the exhaled air is held substantially constant.

OPERATION OF THE EMBODIMENTS OF FIGS. 1 AND 2

Initially, the corrugated tube 12 is connected to the respiratory apparatus on the patient so that exhaled gas from the patient passes through this tube 12 through the inlet opening 11 into the manifold 10. The oxygen tank 19 is turned on to supply the driving gas to the inlet port 13 of the venturi 23. Oxygen is conveniently used since it is available under pressure and is free of moisture or other particulates; that is, it is essentially sterilized. It should be understood, however, that compressed air could be used as well.

With the driving oxygen gas passing through the venturi 23, there will be developed in the absence of any exhaled gas passing through the corrugated tube 12 and the inlet opening 11 a negative pressure as a consequence of withdrawing of air in the manifold through the induction ports 24. This negative pressure will result in the diaphragm 22 seating against the seat 21 and will also result in the diaphragm 27 for the switch 16 moving away from the reed switch 25 so that the reed switch 25 opens. Thus, when the diaphragms 22 and 27 are in their dotted line positions 22' and 27' there is a negative pressure within the manifold 10.

Assume now that the patient starts to exhale. The exhaled gas will pass through the opening 11 and immediately the pressure in the central chamber 20 of the manifold 10 will become essentially ambient pressure. The diaphragm 22 will assume its open solid line position as the exhaled gas passes into the manifold and thence starts to be collected in the flaccid bag 15. The direction of exhaled air flow is indicated by the arrows in FIG. 2.

Simultaneously with the movement of the diaphragm 22 to open position, the diaphragm 27 will move to its solid line position thereby positioning the magnet 26 adjacent to the reed switch 25 closing the same. Closure of the reed switch 25 starts the timer 17.

The exhaled gas collected in the flaccid bag 15 and in the central chamber 20 is continuously withdrawn by the venturi 23 through the induction ports 24 as also indicated by the arrows. When exhalation has been completed by the patient, there will no longer be a flow of exhaled gas into the manifold 10 through the inlet opening 11. However, the exhaled gas collected in the bag 15 will still be flowing through the venturi and accordingly, the ambient pressure in the central chamber 20 will remain essentially at a constant value. However, as soon as the collected exhaled air in the bag 15 is exhausted, and the venturi continues to operate, there will then develop a negative pressure in the central chamber 20 thereby causing closure of the diaphragm 22 against the valve seat 21. This closure results in a further negative pressure being developed sufficient to pull the diaphragm 27 and magnet 26 away from the reed switch 25 thereby stopping the timer 17.

A signal is developed by the timer and digitally displayed which constitutes a function of the total time period taken to exhaust the exhaled gas. Since the conditions are such as to result in a substantially constant flow of the exhaled gas out through the venturi, the total length of time for such constant flow is also a direct function of the volume of exhaled gas. Thus, the digital display 18 in FIG. 12 can be calibrated to display volumetric units such as milliliters indicative of the total volume of exhaled gas.

As mentioned heretofore, by providing the partition 28 with the orifice 29, the flow of the exhaled gas to the venturi through the orifice is at a fairly constant flow rate so that accuracy is assured in the display of volumetric units as determined by the period of time measured for the overall flow.

When the patient next starts to exhale, the diaphragm 22 is then moved to the right as viewed in FIG. 2 and the diaphragm 27 moved upwardly since the pressure then reverts from its previous negative value to ambient value. The reed switch 25 is again closed which action will reset the timer and a new cycle is started.

From the foregoing, it will be clear that a volumetric reading is instantly displayed of the exhaled air.

In FIG. 2 there is shown on top of the digital display 18 an audible alarm schematically indicated by the loudspeaker 34 responsive to a signal generated in an appropriate unit 35 adjustable by knob 36. Adjustable knob 36 enables adjustment of a predetermined volume in the unit 35; for example, 350 milliliters as displayed. The unit 35 is such that if a measured volume of exhaled gas is less than 350 milliliters at any one point and this is repeated over a period of 30 seconds or so, then an alarm is sounded by the speaker 34 providing a warning that a critical condition exists in the respiration of the patient.

DESCRIPTION OF THE EMBODIMENT OF FIG. 3

Figure 3:
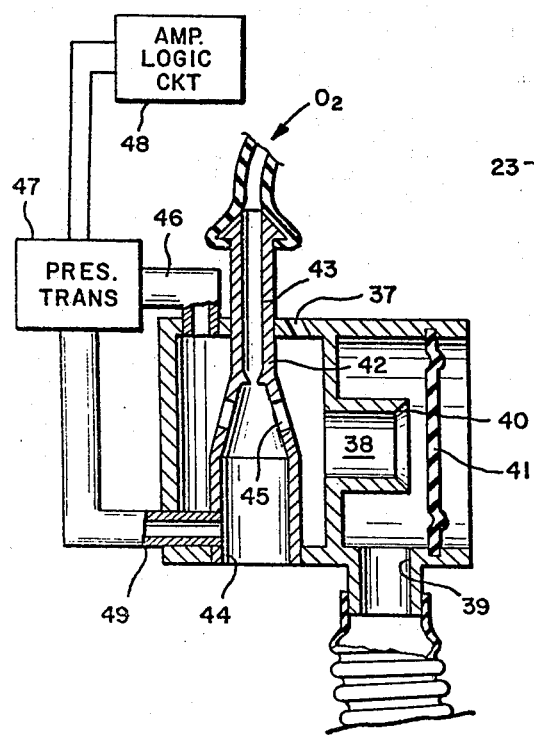

Referring now to FIG. 3, there is shown another embodiment of the invention wherein the flaccid bag 15 is eliminated and a modified type of pressure responsive indicating means is used. The apparatus of FIG. 3 is most useful in diagnostic operation.

Specifically, the structure of FIG. 3 again includes a manifold 37 provided with a central chamber 38. Again, there is provided an inlet opening 39 for receiving exhaled gas from a patient. Also, there is provided a pressure responsive valve in the form of valve seat 40 cooperating with a diaphragm 41.

As with the structure described in FIG. 2, a venturi is provided in the central chamber 38 at 42 in FIG. 3. Venturi 42 receives driving gas through an inlet port 43 and expels this gas outside the manifold 37 through outlet port 44. Induction ports 45 within the manifold 37 serve to draw exhaled gas from the central chamber 38.

A pressure sensor indicated by conduit 46 adjacent to the venturi 43 in the central chamber 38 is provided connecting to a pressure transducer 47. Pressure transducer 47 transduces the pressure into an electrical signal which is passed to a logic circuit indicated by the block 48.

As an optional feature, the embodiment of FIG. 3 may also include a second pressure sensor indicated by the conduit 49 positioned at the downstream end of the venturi 42 at the mouth of the venturi. This pressure sensor 49 also connects to the pressure transducer 47, and if desired, the pressure transducer 47 can be made into a differential pressure transducer for providing a signal constituting a function of the difference between the pressure sensed by the sensor 46 and the sensor 49.

OPERATION OF THE EMBODIMENT OF FIG. 3

In operation, the venturi 42 is provided with driving gas in the form of oxygen as in the other embodiment. This flow of driving gas creates a given pressure sensed at 46 as well as another pressure sensed at 49. These pressures are converted into an electrical signal in the pressure transducer 47.

If now a patient exhales into the inlet opening 39, there will be a change in the sensed pressures both at 46 and 49 as a consequence of the increased gas pressure within the central chamber 38 in the manifold 37, this exhaled gas being inducted through the ports 45 into the venturi. This change in pressure will result in a change or modulation of the signal output from the pressure transducer at a given point in time.

After exhalation has been completed, there will again be a change in the pressure sensed at 46 and 49 giving rise to another modulated output signal from the pressure transducer 47. This second output signal indicates the end or completion of exhalation and can be utilized with respect to the first sensed change in pressure to again define a given time interval which will be directly proportional to the volume of exhaled gas. Also, the pressure signals will provide an indication of flow rate and in fact the pressure difference between the sensed pressures at 46 and 49 provide a continuous indication of flow rate through the venturi. Thus, this flow rate can be integrated in the logic circuit 48 as a means also of indicating the total volume of exhaled gas.

While not shown in FIG. 3, a digital display could be provided responsive to an appropriate signal from the logic circuit 48.

From the foregoing description, it will now be evident that the present invention has provided a greatly improved exhalation monitoring apparatus wherein accuracy is assured and the provision of large digital read out information enables easy operation by unskilled personnel.

Various changes falling within the scope and spirit of this invention will occur to those skilled in the art. The exhalation monitoring apparatus accordingly is not to be thought of as limited to the specific structure set forth merely for illustrative purposes.

I claim:

1. An exhalation monitoring apparatus including, in combination:
    (a) a manifold having a central chamber and an inlet opening for receiving exhaled gas from a patient;
    (b) a flaccid bag connected to said chamber for collecting exhaled gas without appreciably affecting the pressure in said chamber;
    (c) a pressure responsive valve means positioned between said inlet opening and said central chamber responsive to a chamber pressure below ambient pressure to close;
    (d) a venturi in said chamber having an inlet port for connection to a source of driving gas outside said manifold, an outlet port for venting driving gas outside said manifold and an induction port at the throat of the venturi communicating with said chamber for drawing in exhaled gas received through said inlet opening;
    (e) a partition in said chamber between said venturi and the interior chamber portion in communication with the flaccid bag, said partition having a fixed orifice through which exhaled air is passed to the venturi so that the flow rate of said exhaled air passing into the induction port of said venturi is held substantially constant by said orifice; and
    (f) pressure responsive means including an electrical switch means, timer and digital display, said electrical switch means closing to start the timer in response to the pressure in said chamber changing from a negative value to ambient pressure as a result of exhaled gas being received into said chamber, and responsive to the pressure in said chamber changing back to a negative value as a result of all of said exhaled gas having been exhausted from said chamber by said venturi to terminate operation of said timer, said timer providing a signal defining the length of time the pressure switch means is closed to thereby define the volume of exhaled gas, said digital display being responsive to said signal to indicate said volume in volumetric units.

2. An apparatus according to claim 1, including an audible alarm responsive to the volume of exhaled gas falling below a given value to provide a warning of a critical condition.

* * * * *